US008435541B2

(12) United States Patent
Ceccoli et al.

(10) Patent No.: US 8,435,541 B2
(45) Date of Patent: May 7, 2013

(54) TOPICAL COMPOSITIONS FOR INHIBITING MATRIX METALLOPROTEASES AND PROVIDING ANTIOXIDATIVE ACTIVITIES

(75) Inventors: Joseph D. Ceccoli, Farmingville, NY (US); Brian Costello, Port Jefferson Station, NY (US); James A. Hayward, Stony Brook, NY (US); Konstantinos M. Lahanas, Paramus, NJ (US)

(73) Assignee: Bath & Body Works Brand Management, Inc., Reynoldsburg, OH (US)

( * ) Notice: Subject to any disclaimer, the term of this patent is extended or adjusted under 35 U.S.C. 154(b) by 53 days.

(21) Appl. No.: 12/874,884

(22) Filed: Sep. 2, 2010

(65) Prior Publication Data
US 2012/0058140 A1 Mar. 8, 2012

(51) Int. Cl.
A61K 8/97 (2006.01)
(52) U.S. Cl.
USPC ...... 424/195.15; 424/401; 424/757; 424/739; 424/729; 424/765; 514/18.8; 514/21.8
(58) Field of Classification Search .................. None
See application file for complete search history.

(56) References Cited

U.S. PATENT DOCUMENTS

| | | | |
|---|---|---|---|
| 4,129,644 A | 12/1978 | Kalopissis et al. |
| 4,279,812 A | 7/1981 | Cioca |
| 4,285,986 A | 8/1981 | Cioca et al. |
| 4,363,760 A | 12/1982 | Cioca |
| 4,374,121 A | 2/1983 | Cioca |
| 4,415,628 A | 11/1983 | Cioca et al. |
| 4,419,288 A | 12/1983 | Cioca |
| 4,497,862 A | 2/1985 | Cioca et al. |
| 4,515,637 A | 5/1985 | Cioca |
| 4,585,797 A | 4/1986 | Cioca |
| 4,590,022 A | 5/1986 | Cioca et al. |
| 4,591,501 A | 5/1986 | Cioca |
| 5,073,371 A | 12/1991 | Turner et al. |
| 5,073,372 A | 12/1991 | Turner et al. |
| 5,080,900 A | 1/1992 | Stanley |
| 5,114,953 A | 5/1992 | Galardy et al. |
| 5,183,900 A | 2/1993 | Galardy et al. |
| 5,189,178 A | 2/1993 | Galardy et al. |
| 5,239,078 A | 8/1993 | Galardy et al. |
| 5,268,384 A | 12/1993 | Galardy |
| 5,270,326 A | 12/1993 | Galardy et al. |
| 5,547,672 A | 8/1996 | Xiu |
| 5,616,325 A | 4/1997 | Xiu |
| 5,650,137 A | 7/1997 | Nguyen et al. |
| 5,696,147 A | 12/1997 | Galardy |
| 5,773,438 A | 6/1998 | Levy et al. |
| 5,837,224 A | 11/1998 | Voorhees et al. |
| 5,892,112 A | 4/1999 | Levy et al. |
| 5,997,875 A | 12/1999 | Zhou et al. |
| 6,130,254 A | 10/2000 | Fisher et al. |
| 6,162,458 A | 12/2000 | Asada et al. |
| 6,451,329 B1 | 9/2002 | Sandewicz et al. |
| 6,645,502 B2 | 11/2003 | Sandewicz et al. |
| 6,713,074 B2 | 3/2004 | Lerner et al. |
| 6,803,032 B2 | 10/2004 | McCaulley et al. |
| 6,841,153 B1 | 1/2005 | Chegini et al. |
| 6,906,036 B2 | 6/2005 | Quirk et al. |
| 7,014,870 B1 | 3/2006 | Hon et al. |
| 7,071,167 B2 | 7/2006 | Renault |
| 7,087,259 B2 | 8/2006 | Wild et al. |
| 7,094,754 B2 | 8/2006 | Quirk et al. |
| 7,105,184 B2 | 9/2006 | Pauly et al. |
| 7,314,634 B2 * | 1/2008 | Hernandez et al. ........... 424/401 |
| 7,354,926 B2 | 4/2008 | Lintner |
| 7,507,750 B2 | 3/2009 | Nishimura et al. |
| 7,666,442 B2 | 2/2010 | Morariu |
| 2003/0170265 A1 | 9/2003 | Henry et al. |
| 2004/0121031 A1 | 6/2004 | Majeed et al. |
| 2005/0063932 A1 | 3/2005 | Dilallo et al. |
| 2005/0186168 A1 | 8/2005 | Albin |
| 2006/0074108 A1 | 4/2006 | Gupta |
| 2006/0165643 A1 | 7/2006 | Lintner |
| 2006/0251750 A1 | 11/2006 | Tabor |
| 2007/0065396 A1 | 3/2007 | Morariu |
| 2007/0065415 A1 | 3/2007 | Kleinsek et al. |
| 2007/0122492 A1 | 5/2007 | Behr et al. |
| 2008/0213202 A1 * | 9/2008 | Maes et al. ...................... 424/59 |

FOREIGN PATENT DOCUMENTS

CA 2539712 9/2007
WO WO2007030975 3/2007

OTHER PUBLICATIONS

Lee (Journal of Dermatological Science (2005), vol. 40, pp. 195-204).*
J.F. Woessner, et al., Matrix Metalloproteinases and TIMPs, 2000, Ed. 2, Oxford University Press, USA.
Jong Hee Lee, et al., (Abstract) The Effects of Epigallocatechin-3-gallate on Extracellular Matrix . . . , Journal of Dermatological Science, Dec. 2005, 195-204, 40(3), USA.
Peter A. Hill, et al., Inhibition of Bone Resorption in Vitro by Selective Inhibitors of Gelatinase and Collaginase, Biochemical Journal, 1995, 167-75, 308, USA.
Laura Mattila et al., Activation of Tissue Inhibitor of Metalloproteinases-3 (TIMP-3) mRNA . . . , The Journal of Investigative Dermatology, Apr. 1998, 416-21, 110(4), USA.
Kanako Kikuchi et al., Tissue Inhibitor of Metalloproteinase 1 (TIMP-1) May be an Autocrine . . . , The Journal of Investigative Dermatology, Mar. 1997, 281-84, 108(3), USA.
Hironobu Ihn, et al., IL-4 Up-Regulates the Expression of Tissue Inhibitor of Metalloproteinase-2 . . . , The Journal of Immunology, Feb. 2002, 1895-902, 168, USA.

(Continued)

*Primary Examiner* — Susan Hoffman
(74) *Attorney, Agent, or Firm* — Andrus, Sceales, Starke & Sawall, LLP

(57) ABSTRACT

A topical composition according to the present invention for use in a skin care regimen that provides matrix metalloprotease (MMP) inhibiting activity, tissue inhibitor of metalloprotease (TIMP) inducing activity, and immediate and delayed antioxidative activity. Preferably, the topical composition comprises at least one MMP inhibitor, a TIMP inducing agent, *Tremella fuciformis* (snow fungus) extract, *Camellia sinensis* (green tea) leaf extract, and *Eugenia caryophyllus* (clove) extract. The compositions are useful in anti-wrinkle and anti-aging products, providing elasticity, firmness, tone and texture to the skin, ameliorating fine lines and preventing skin damage.

11 Claims, 2 Drawing Sheets

OTHER PUBLICATIONS

Praveen K. Vayalil, et al., Green Tea Polyphenols Prevent Ultraviolet Light-Induced Oxidative Damage . . . , Journal of Invenstigative Dermatology, 2004, 1480-87, 122, USA.

H.P. Zhou et al., (Abstract in English and Chinese) Anti-Aging Effect of the Polysaccharides from . . . , Journal of China Pharmaceutical University, 1989, 303-6, 20, China.

Qi-Long Ying, et al., Inhibition of Human Leucocyte Elastase by Ursolic Acid, Biochemistry Journal, 1991, 512-16, 277, USA.

J. Liu, (Abstract) Pharmacology of Oleanolic and Ursolic Acid, Journal of Ethnopharmacology, 1995, 57-68, 49, USA.

Ilhami Gülçin, et al., Comparison of Antioxidant Activity of Clove (*Eugenia caryophylata* Thunb) Buds and Lavender, Food Chemistry, 2004, 393-400, 87, USA.

Guan Wenqiang, et al., Comparison of Essential Oils of Clove Buds Extracted with Supercritical Carbon Dioxide and . . . , Food Chemistry, 2007, 101, 1558-1564, USA.

Kwang-Gwen Lee, et al., Antioxidant Property of Aroma Extract Isolated from Clove Buds [*Syzygium aromaticum* (L.) Merr. et Perry], Food Chemistry, 2001, 443-448, 74, USA.

R.E. Kramer, Antioxidants in Clove, Journal of the American Oil Chemists' Society, Jan. 1985, 111-113, 62(1), USA.

Cloves & Clove Oil http://www.healingnaturallybybee.com/articles/anti1.php, 2008.

Encyclopedia of Spices: Cloves http://www.theepicentre.com/Spices/cloves.html, 2008.

Jos B. G. Paquay, et al., Protection Against Nitric Oxide Toxicity by Tea, Journal of Agricultural and Food Chemistry, 2000, 5768-5772, 48(11), USA.

Mariken J. T. J. Arts, et al., Interactions Between Flavonoids and Proteins: Effect on . . . , Journal of Agricultural and Food Chemistry, 2002, 1184-1187, 50(5), USA.

Nan-Yin Chen, et al., Effects of Cytokine-Stimulating Activities of EPS from *Tremella mesenterica* with Various Carbon Sources, Food Chemistry, 2006, 92-97, 99, USA.

Patrick Poucheret, et al., Biologocal and Pharmacological Activity of Higher Fungi: 20-Year Retrospective Analysis, Cryptogamie, Mycologie, 2006, 311-333, 27(4), Frace.

Mary P. Lupo, Cosmeceutical Peptides, Dermatologic Surgery, 2005, 832-836, 31(7) Part 2, USA.

Mary P. Lupo, Peptides for Facial Skin Aging, Simplified Facial Rejuvenation, 2008, Chapter 7, Springer Berlin Heidelberg New York.

Bin Shan, et al., Antioxidant Capacity of 26 Spice Extracts and Characterization of Their Phenolic . . . , Journal of Agricultural and Food Chemistry, 2005, 7749-7759, 53, USA.

Yizhong Cai, Antioxidant Phenolic Constituents in Roots of Rheum officinale and *Rubia cordifolia* . . . , Journal of Agricultural and Food Chemistry, 2004, 7884-7890, 52, USA.

S. Omar, et al., Antimicrobial Activity of Extracts of Eastern North American Hardwood Trees and Relation to . . . , Journal of Ethnopharmacology, 2000, 161-170, 73.

Engelhard EquiStat® Advanced Anti-Aging Complex, 2005.

Bath and Body Works® Patricia Wexler M.D.® Dermatology MMPi20 Skin Regenerating Serum 3.4 oz, accessed Dec. 16, 2012.

Details for European Commission Ingredient: Acetyl Hexapeptide-20, Jul. 31, 2012, http://ec.europa.eu/consumers/cosmetics/cosing/index.cfm?fuseaction=search.details&id=83677.

INCI Directory for Hexapeptide-20, Jul. 31, 2012, http://www.specialchem4cosmetics.com/services/inci/ingredient.aspx?id=5538.

\* cited by examiner

TOPICAL COMPOSITIONS FOR INHIBITING MATRIX METALLOPROTEASES AND PROVIDING ANTIOXIDATIVE ACTIVITIES

FIELD OF THE INVENTION

The present invention generally relates to a composition for topical application. Specifically, a cosmetic or dermapharmaceutical composition is provided for antioxidative activities and immediate and delayed inhibition of matrix metalloprotease (MMPs) upon topical application thereof and thereby reducing and preventing wrinkles and damage of the skin.

BACKGROUND OF THE INVENTION

Lines and wrinkles on the skin are caused by degenerative changes in the proteins of the dermal extracellular matrix. They are signs of both chronologically-aged and photo-aged skin. In the past years, chronological aging and photo-aging were classified as different phenomena. However, in recent years, researchers have discovered some common molecular mechanisms between the two. Such mechanisms include decreased synthesis of new collagen, decreased anti-oxidative activities, and increased amount of matrix metalloproteases (MMPs).

MMPs are members of the zinc-dependent endopeptidases family. To date, there are over twenty known MMPs, each labeled in a general format "MMP-x," wherein $x \geq 1$. The MMP gene family can be divided according to their substrate specificity and structure into subgroups of collagenases, gelatinases, stromelysins, matrilysin, enamelysin, membrane-type MMP, and others. For example, MMP-1 is a collagenase, MMP-3 is a stromelysin, and MMP-9 is a gelatinase.

One major biological function of MMPs is to catalyze the breakdown of macromolecules in the extracellular matrix such as collagen and elastin. The breakdown of dermal collagen and elastin is purported to be one of the major contributing factors to loss of skin's firmness and elasticity. Such changes cause the skin to appear aged (i.e., dull, wrinkled, and saggy). Thus, it is of great importance to reduce, if not completely block, the enzymatic activity of MMPs.

In fact, human tissues are capable of naturally producing inhibitors of MMPs known as tissue inhibitors of matrix metalloproteases (TIMPs). At present, the TIMP gene family consists of four members: TIMP-1, TIMP-2, TIMP-3, and TIMP-4. TIMPs are capable of reversibly inhibiting the MMPs in a 1:1 stoichiometric fashion. A more detailed and comprehensive review of MMPs and TIMPs has been presented by Woessner and Nagase in *Matrix Metalloproteinases and TIMPs*, Oxford University Press, 2000. In addition to their inhibitory role against MMPs, TIMPs are also able to promote cell proliferation in a wide range of cell types and may have an anti-apoptotic function. This indicates that TIMPs may be able to serve as MMP inhibitors as well as skin regenerators. Unfortunately, the biological production of TIMPs decreases with aging, while the production of MMP increases, thereby contributing to the aging of the skin. Thus, it is desirable to supplement the depleted TIMPs by delivering to the skin inhibitors of MMP.

To date, a number of agents have been studied for their potency as MMP inhibitors. For example, it has been demonstrated that the topical application of epigallocatechin-3-gallate or retinoic acid to a skin tissue model prior to UVA irradiation prevents an increase in MMP-1 (interstitial collagenase) expression and activity. (Jong Hee Lee, et al., *The Effects of Epigallocatechin-3-gallate on Extracellular Matrix Metabolism*, Journal of Dermatological Science, 40(3); 195-204 (December 2005)). Similarly, 2',4',7-trihydroxyisoflavone, also prevents increases in UV-induced MMP-1 activity in cultured fibroblasts. Other examples of MMP inhibitors are described and studied as CT1166 and RO31-7467 by Hill et al. (Peter A. Hill, et al., *Inhibition of Bone Resorption In Vitro by Selective Inhibitors of Gelatinase and Collaginase*, Biochemical Journal, 308; 167-175 (1995)).

Of the MMP inhibitors studied, some are used in topical cosmetic compositions to counteract the effect of photo- and chronological skin aging. For example, certain di-peptide analogs with fused or conjugated bicycloaryl substitutes are potent broad-spectrum hydroxamate inhibitors of MMPs. One example of such di-peptides is Galardin (INCI name: N-[(2R)-2-(hydroxamidocarbonylmethyl)-4-methylpentanoyl]-L-tryptophan methylamide), the structure of which is shown below:

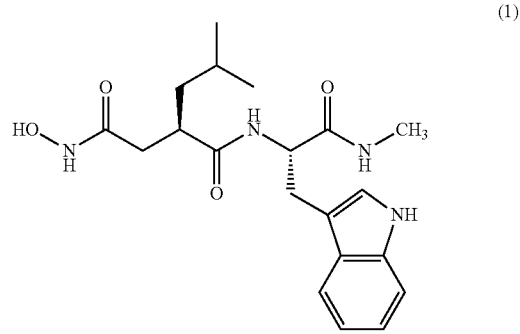 [SMILES: CNC(=O)[C@H](Cc1c[nH]c2ccccc12)NC(=O)[C@@H](CC(=O)NO)CC(C)C]

(1)

Galardin inhibits MMP activities by interacting with the zinc atom in the active site of MMPs. Another example of commercially available MMP inhibitor is Pepha®-TIMP available from Pentapharm AG. Pepha®-TIMP is TIMP-2 which exhibits strong inhibitory effect towards MMP-1, but also effective against MMP-2, MMP-3, MMP-8, and MMP-9.

Furthermore, the use of MMP inhibitors in combination with other anti-aging cosmetic agents is known in the art. For example, the use of UV blockers (e.g. octinoxate and zinc oxide) in combination with an MMP inhibitor for inhibiting photoaging of skin is known. Cosmetic compositions including an MMP inhibitor and a natural estrogen (e.g., 17-beta estradiol or an estrogen-like steroid) have also been reported to diminish skin wrinkles and fine lines.

Another example of agents known to be combined with MMP inhibitors is antioxidants. Antioxidants are molecules or complexes that are capable of slowing or preventing the oxidation of other biomolecules caused by free radicals and reactive oxygen species. Damages to healthy cells caused by such harmful agents are a major contributor to wrinkles and precancerous cell changes in the skin. In fact, human body is capable of producing natural antioxidants. One example is superoxide dismutase ("SOD"), an enzyme that neutralizes superoxide free radical ($.O_2^-$), which is the most common free radical in the body that can damage other important enzymes, membrane lipids, and nucleic acids. Additionally, SOD promotes cell repair and production of functional fibroblasts in the dermis. However, the SOD levels decrease with age. Thus, much of dermapharmaceutical compositions known in the art have been combining MMP inhibitors and antioxidants in an effort to replenish the body's deficiency of such anti-aging agents.

However, a common shortcoming of aforementioned cosmetic compositions comprising MMP inhibitors and anti-aging agents is that they provide short-term MMP inhibitory and antioxidative activities. Such compositions temporarily reverse or reduce the skin damage caused by MMPs, but they must be frequently reapplied to the skin for a lasting anti-aging effect. This is impractical and uneconomical from the consumers' perspective. Thus, researchers are now looking to agents with long-term anti-aging effect that stimulate the body's production of endogenous MMP inhibitors (i.e., TIMPs) and/or SOD.

The up-regulation of TIMP gene in the skin is considered as a form of long-term "anti-aging" mechanism, because an increase in the number of TIMPs contributes to the reduction of MMPs' destructive activities. The human body is capable of up-regulating the expression of TIMP genes by various cytokines. For example, the production of TIMP-1 and TIMP-3 are enhanced by a cytokine called Transforming Growth Factor beta (TGF-β). (Laura Mattila et al., *Activation of Tissue Inhibitor of Metalloproteinases-3 (TIMP-3) mRNA Expression in Scleroderma Skin Fibroblasts*, The Journal of Investigative Dermatology, 110(4); 416-421 (April 1998); and Kanako Kikuchi et al., *Tissue Inhibitor of Metalloproteinase 1 (TIMP-1) May be an Autocrine Growth Factor in Scleroderma Fibroblasts*, The Journal of Investigative Dermatology, 108(3); 281-284 (March 1997)). TIMP-2 has been shown to be induced by another type of cytokine called interleukin-4 (IL-4). (Ihn et al., *IL-4 Up-Regulates the Expression of Tissue Inhibitor of Metalloproteinase-2 in Dermal Fibroblasts via the p38 Mitogen-Activated Protein Kinase-Dependent Pathway*, The Journal of Immunology, 168; 1895-1902 (February 2002)). However, products providing such long-term effects alone are inadequate to attract consumers who are interested to see immediate results.

Thus, it is desirable to provide a topical composition that provides a long-term anti-aging benefits to the skin comprising an agent that induces TIMP production ("TIMP inducing agent") and an agent that induces SOD production ("SOD inducing agent"). There is also a need for a topical composition that further provides short-term anti-aging benefits to the skin comprising an MMP inhibitor. Similarly, there is a need for topical composition that incorporates SOD inducing agents and antioxidants for both a long-term and short-term protection from free radical damage to the skin. During our endeavor to create an effective anti-aging composition having long-term and short-term anti-aging effects, it has been unexpectedly discovered that the combination of an MMP inhibitor(s), a TIMP inducing agent(s), an antioxidant(s), and an SOD inducing agent(s) provides a remarkably synergistic antioxidative and MMP inhibitory activity, thereby providing powerful anti-aging effects on the skin.

SUMMARY OF THE INVENTION

The present invention is directed toward topical compositions that diminish skin wrinkles, fine lines and improve skin tones. More specifically, the present invention provides topical compositions for use as a topical skin care regimen that preferably combine at least one matrix metalloprotease inhibitor ("MMP inhibitor") component, at least one tissue inhibitor of metalloprotease ("TIMP") inducing agent, and at least one natural extract, such as a plant, fungus, and/or fruit extract. Such combination of agents provides synergistic anti-aging effects to the skin. More preferably, the MMP inhibitor component comprises *Glycine soja* (soybean) seeds extract, TIMP inducing agent comprises acetyl hexapeptide-20, and the natural extract is selected from the group consisting of *Tremella fuciformis* (snow fungus) extract, *Eugenia caryophyllus* (clove) extract and *Camellia sinensis* (green tea) extract, *Pyrus malus* (apple) fruit extract, *Cinnamomum cassia* (cinnamon) Bark extract, *Rheum palmatum* (Chinese rhubarb) extract, and combinations thereof.

Without being limited thereto, the topical composition of the present invention may be in the form of gel, lotion, oil-in-water or water-in-oil emulsions, water-in-silicone emulsions, hydroalcoholic systems, aerosol, spray or anhydrous form.

It is an object of the present invention to provide topical compositions that provide short-term MMP inhibiting and antioxidative activities.

It is another object of the present invention to provide topical composition that stimulates the body's production of TIMP and superoxide dismutase (SOD), promoting long-term anti-aging effects.

It is another object of the present invention to provide topical composition that provides long-term antioxidative activities.

It is another object of the present invention to provide topical compositions having at least one MMP inhibitor.

It is another object of the present invention to provide topical composition that is effective to inhibit a broad spectrum of matrix metalloprotease, including MMP-1, MMP-3 and MMP-9.

It is another object of the present invention to provide topical compositions having a tissue inhibitor of matrix metalloprotease (TIMP) inducing agent.

It is another object of the present invention to provide topical compositions comprising various natural extracts providing antioxidative and MMP inhibiting effects.

It is another object of the present invention to provide topical compositions having at least one MMP inhibitor, a TIMP inducing agent, and natural extract component having high concentration of antioxidants.

It is another object of the present invention to provide topical compositions for use in anti-wrinkle and/or anti-aging cosmetic compositions.

It is another object of the present invention to provide topical compositions that provide elasticity, firmness, tone and texture to the skin.

It is another object of the present invention to provide topical compositions that ameliorate fine lines and prevent photo-damage of the skin.

BRIEF DESCRIPTION OF THE FIGURES

A further understanding of the present invention can be obtained by reference to a preferred embodiment, along with some alternative embodiments, set forth in the illustrations of the accompanying figures. Although the illustrated embodiments are merely exemplary of systems for carrying out the present invention, the organization and method of operation of the invention in general, together with further objectives and advantages thereof, may be more easily understood by reference to the figures and the following description. The figures are not intended to limit the scope of this invention, which is set forth with particularity in the claims as appended or as subsequently amended, but merely to clarify and exemplify the invention.

For a more complete understanding of the present invention, reference is now made to the following figures.

DETAILED DESCRIPTION OF THE INVENTION

Figure 1:
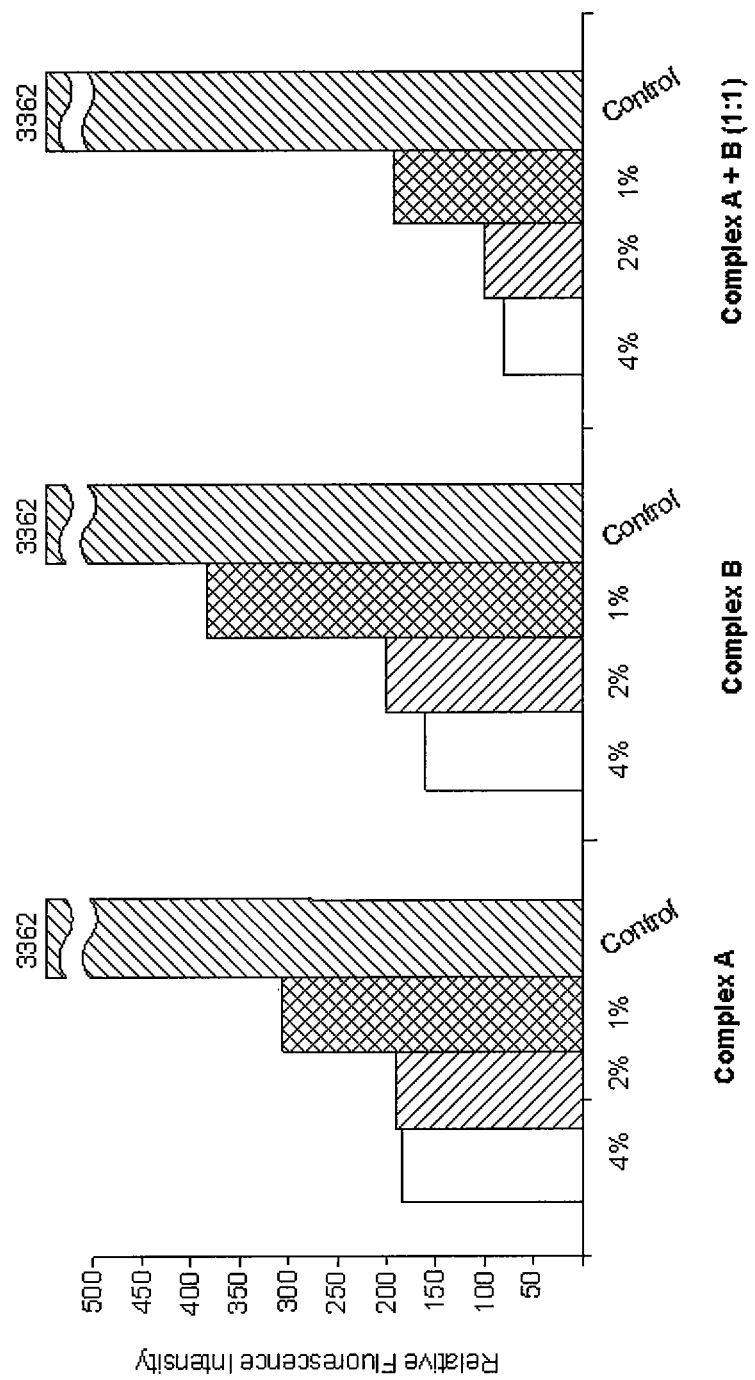
FIG. 1 illustrates a histogram representing the MMP inhibiting effect of a composition comprising an MMP inhibitor and natural extracts, a composition comprising a TIMP inducing agent and natural extracts, and the effect of a combination thereof in a 1:1 ratio.

Detailed illustrative embodiments of the present invention are disclosed herein. However, the present invention may be embodied in a wide variety of forms, some of which may be quite different from those in the disclosed embodiments. Consequently, the specific ingredients and functional details disclosed herein are merely representative, yet in that regard, they are deemed to afford the best embodiments for purposes of disclosure and to provide a basis for the claims herein which define the scope of the present invention.

Moreover, well known methods and procedures for both carrying out the objectives of the present invention and illustrating the preferred embodiments are incorporated herein by reference but have not been described in detail as not to unnecessarily obscure aspects of the present invention.

The present invention relates to topical compositions providing short-term and long-term anti-aging effects to the skin. By combining an MMP inhibitor component and a TIMP inducing agent in the topical composition, the present invention promotes skin's short-term healing, as well as body's natural generation of TIMPs for prolonged MMP inhibiting effects. Furthermore, the incorporation of natural extract component in the present invention aids in the synergic anti-aging effects of the topical compositions. Therefore, the topical composition restores photo-aged and chronologically-aged skin by providing elasticity, firmness, tone and texture to the skin, while ameliorating fine lines and wrinkles.

MMP Inhibitor Component

The MMP inhibitor component of the topical composition comprises at least one MMP inhibitor that provides a short-term anti-aging effect. The amount of the MMP inhibitor component may be adjusted such that a final cosmetic product comprises from about 0.001% to about 1.0% by weight of the MMP inhibitor component. It is contemplated that MMP inhibitors encompass various agents that are capable of directly or indirectly retarding the catabolic function of at least one type of MMP. Preferably, the topical composition of the present invention comprises an MMP inhibitor that is effective to inhibit a broad spectrum of MMP, including MMP-1, MMP-3 and MMP-9. Furthermore, the MMP inhibitors need not completely inhibit the activity of target MMPs to be effective. It is enough that some inhibition of the target MMPs occurs.

Preferably, the MMP inhibitor component comprises *Glycine soja* (soybean) seeds extract, which contains a soy peptide complex. The soy peptide complex has been specially formulated to provide maximal MMP inhibitory activity. The soy peptide complex is effective for inhibiting at least MMP-1, MMP-3, and MMP-9 and prevents these MMPs from degrading dermal macromolecules, such as collagen and elastin. The soy peptide complex also provides essential amino acids for the synthesis of skin collagen and interacts synergistically with other components to improve skin conditions and provide anti-aging benefits.

Other commercially available MMP inhibitors that may be useful in the topical composition of the present invention may be used. For example, Galardin (INCI name: N-[(2R)-2-(hydroxamidocarbonylmethyl)-4-methylpentanoyl]-L-tryptophan methylamide) is a dipeptide MMP inhibitor that directly interacts with the active sites of MMPs. On the other hand, other types of MMP inhibitors, such as farnesyl transferase inhibitors (farnesyl acetate and (α-hydroxyfarnesyl) phosphoric acid) prevent expression of certain MMPs by interfering with signal transduction pathways for UVB-inducible MMPs (U.S. Pat. No. 5,837,224). Other commercially available MMP inhibitors that may be used in the topical composition of the present invention include, but are not limited to Batimastat (IUPAC name: (2S,3R)—N-hydroxy-N'-[(1S)-1-(methylcarbamoyl)-2-phenyl-ethyl]-3-(2-methylpropyl)-2-(thiophen-2-ylsulfanylmethyl)butanediamide), Marimastat (IUPAC name: N-[2,2-dimethyl-1-(methylcarbamoyl)propyl]-2-[hydroxy-(hydroxycarbamoyl)methyl]-4-methyl-pentanamide), Galardin (INCI name: N-[(2R)-2-(hydroxamidocarbonylmethyl)-4-methylpentanoyl]-L-tryptophan methylamide), Colhibin (INCI name: hydrolyzed rice protein, glycerin, water), Pepha®-TIMP (INCI name: Tissue Inhibitor of Metalloproteinases 2), Syn®-Coll (INCI name: palmitoyl tripeptide-5, glycerine), Trylagen® (INCI name: water, *Pseudoalteromonas* ferment extract, hydrolyzed wheat protein, hydrolyzed soy protein, tripeptide-10 citrulline, tripeptide-1, Lecithin, xantham gum, carbomer, triethanolamine, caprylyl glycol), Ilomastat (INCI name: N-[(2R)-2-(hydroxamidocarbonylmethyl)-4-methylpentanoyl]-L-tryptophan methylamide), and combinations thereof. Marimastat and Batimastat are available from British Biotech Ltd. Colhibin, Pepha®-TIMP, and Syn®-Coll are available from Pentapharm AG. Trylagen® can be purchased from Lipotec, S.A. and Ilomastat is available from Chemicon International, Inc. Further examples of MMP inhibitors are those disclosed in U.S. Pat. Nos. 5,183,900, 5,189,178, 5,239,078, 5,696,147, 5,837,224, 5,773,438, and 5,892,112, all of which are incorporated herein by reference.

Natural Extract Component

The topical composition of the present invention further comprises a natural extract component. The natural extract component may comprise an extract derived from a plant, fruit, fungus, or a mixture thereof. The amount of a natural extract component may be adjusted such that a final cosmetic product comprises from about 1.0% to about 25% by weight of natural extract component. The natural extract component preferably has high antioxidative capacity, MMP inhibitory activity, and SOD inducing ability, thereby providing both short-term and long-term anti-aging benefits to the skin. The short-term anti-aging effects are caused by agents that are antioxidants and/or MMP inhibitors. Antioxidative agents often contain effective reducing agents such as polyphenols, glutathione, vitamin C, and vitamin E. The long-term antioxidative benefits are provided by certain agents that are capable of either stimulating the production of body's endogenous antioxidants (e.g. superoxide dismutase) or enhancing the activity of such endogenous antioxidants. The natural extract(s) used in the present invention may be obtained through conventional methods known in the art, such as solvent extraction, distillation, enfleurage, and ram press method.

Preferably, the natural extract component may comprise *Eugenia caryophyllus* (clove) extract. Clove extract not only acts as a MMP inhibitor, but also believed to be one of nature's most powerful antioxidant. *Eugenia caryophyllus* (clove) extract is an example of the short-term anti-aging agent. It is preferably prepared by liquid extraction in glycerin and water. Clove extract is a potent MMP inhibitor and Human Neutrophil Elastase inhibitor, which in turn protects the extra-cellular matrix from enzymatic degradation. It can be purchased from Biocogent, Ltd. under the trade name Scavenox™ Clove Extract. Clove extract is known to have superior antioxidative effects to most other natural extracts. Major active ingredients in clove extracts include gallic acid derivatives and eugenol/eugenol acetate. Gallic acid acts as an antioxidant and helps to protect cells against oxidative damage. It is found to show cytotoxicity against cancer cells without harming healthy cells. Eugenol and eugenol acetate are main aroma constitutes of clove extract. They are also well known for their antioxidative, anti-fungal, and antimicrobial properties. Combined with the clove extract's potent MMP inhibitory capacity, these activities provide strong anti-inflammatory performance, which enhances the skin texture and ultimately contributes to the overall health of the skin.

Preferably, the natural extract component may further comprise *Camellia sinensis* (green tea) extract. Green tea extract has high content of polyphenols (flavonoids), including gallocatechin, epigallocatechin, epictechin, and epigallocatechin gallate. These polyphenols have been shown to inhibit UVB-induced expression of MMP-2, MMP-3, MMP-7, and MMP-9 in hairless mouse skin. (Praveen K. Vayalil, et al., *Green Tea Polyphenols Prevent Ultraviolet Light-Induced Oxidative Damage and Matrix Metalloproteinases Expression in Mouse Skin*, Journal of Investigative Dermatology, 122: 1480-87 (2004)). Furthermore, green tea extract is a great source of antioxidant. Green tea extract interacts with and inhibits reactive oxidation species (ROS). Comparative UV-lipid peroxidation studies indicate that green tea polyphenols are extremely effective in reducing/inhibiting UV-induced photo-oxidation and protecting cells from free radical damage. As with clove extract, green tea extract used in the present invention is preferably prepared by liquid extraction in glycerin and water. It can be purchased from Biocogent, Ltd. under the trade name Scavenox™ Green Tea Extract.

Preferably, the natural extract component may comprise an extract of *Tremella fuciformis* (snow fungus), also known as white fungus or silver tree-ear fungus—a type of jelly fungus used in Chinese traditional medicine and cuisine. Polysaccharides of *Tremella fuciformis* exert a long-term anti-aging effect by increasing the superoxide dismutase (SOD) production in the skin. (Zhou et al., *Anti-Aging Effect of the Polysaccharides from Auricularia Auricular and Tremella Fuciformis*, Journal of China Pharmaceutical University, 20; 303-6 (1989)). Superoxide dismutase is the body's natural antioxidant for reducing free radical damage to the skin. In U.S. Pat. No. 5,547,672, extracts of the snow fungus have been used as a pharmaceutical agent for treatment of wounds and other skin injuries.

Preferably, the natural extract component may further comprise *Pyrus malus* (apple) fruit extract. Apple fruit extract boosts the antioxidative activities of the cosmetic composition and aids in the synergic anti-aging effects of the topical composition. Apple fruit extract contains powerful anti-inflammatory agents called terpenoids. Terpenoids, such as ursolic acid, inhibit human leukocyte elastase, 5-lipoxygenase, and cyclooxygenase activities. These effects prevent the generation of inflammatory mediators. (Qi-Long Ying et al., *Inhibition of Human Leucocyte Elastase by Ursolic Acid*, Biochemistry Journal, 277; 512-16 (1991)). In addition to its anti-inflammatory properties, ursolic acid also provides amelioration for photo-aged skin by stimulating skin collagen and epidermal cell ceramide synthesis. Ursolic acid helps to reduce the appearance of wrinkles and age spots by restoring the skin's collagen structure and elasticity. A detailed discussion of the mechanism can be found in J. Liu, *Pharmacology of Oleanolic and Ursolic Acid*, Journal of Ethnopharmacology, 49; 57-68 (1995).

Preferably, the natural extract component may further comprise *Cinnamomum cassia* (cinnamon) bark extract. Cinnamon bark extract boosts the antioxidative activities of the cosmetic composition and aids in the synergic anti-aging effects of the topical composition.

Preferably, the natural extract component may further comprise *Rheum palmatum* (Chinese rhubarb) extract. Chinese rhubarb extract boosts the antioxidative activities of the cosmetic composition and aids in the synergic anti-aging effects of the topical composition.

*Quercus rubra* (red oak) bark extract is yet another good source of antioxidant. Red oak bark extract contains tannins, which are readily absorbed into damaged skin. Tannins are highly astringent compounds that act locally by precipitating proteins to the wounds, decreasing cell membrane permeability and exerting anti-inflammatory and anti-bacterial properties. In U.S. Pat. No. 5,080,900, an aqueous extract of oak bark ash has been used for treatment of skin ulcers.

Other examples of natural extracts having antioxidative benefits that may be used in the topical composition of the present invention include, but are not limited to *Ginkgo biloba* extract, Black chokeberry (*Photinia melanocarpa*) extract, Cantaloupe melon (*Cucumis melo* LC., Cucurbitaceae) extract, Bilberry (*Vaccinium myrtillus* L.) extract, French maritime pine (*Pinus pinaster*) extract, Milk thistle (*Silybum marianum*) extract, Caper (*Capparis spinosa* L.) extract, *Culcitium reflexum* leaf extract, *Krameria triandra* root extract, Peach (*Prunus persica*) flower extract, Great burnet (*Sanguisorba officinalis* L.) root extract, Autumn joy (*Sedum telephium*) leaf extract, *Pueraria Lobata* extract, lemon grass extract, basil extract, grape seeds extract, rosemary extract, sage extract, thyme extract, chamomile extract, lavender extract, horse chestnut extract, and lemon extract, *Quercus rubra* (red oak) bark extract, and combinations thereof.

Other examples of natural extracts having both antioxidative and MMP inhibitory activity that may be incorporated into the topical composition of the present invention include, but are not limited to Japanese Horse Chestnut (*Aesculus turbinata Blume*) extract, *Argania spinosa* leaf extract, Pariparoba (*Pothomorphe umbellata*) root extract, Marine eelgrass (*Zostera marina* L.) extract, Pomegranate (*Punica granatum* L.) extract, calaguala (*Polypodium leucotomos*) extract, blackberry (*Rubus fruticosus*) extract, raspberry extract, muscadine grapes extract, rooibos (*Aspalathus linearis*) extract, Pine (*Pinus densiflora*) pollen extract, Blackberry (*Rubus fruticosus*) leaf extract, and combinations thereof. Additionally, U.S. Application Publication No. 2007/0122492 discloses various plant extracts that are capable of inhibiting one or more extracellular proteases including MMP-1, MMP-2, MMP-3, MMP-9. All of such plant extracts are incorporated herein by reference.

Preferably, the composition of the present invention comprises a combination of an MMP inhibitor component and a natural extract component for providing short term antioxidative and MMP inhibiting activities. The relevant amounts of each ingredient may be adjusted such that a final cosmetic product comprises from about 0.001% to about 1.0% by weight of the MMP inhibitor component and from about 1.0% to about 25% by weight of natural extract component. An illustrative example of such combination is PreAge (available from BASF Corporation). PreAge generally comprises *Glycine soja* (soybean) seed extract as the MMP inhibitor component, and *Pyrus malus* (apple) fruit extract, *Cinnamomum cassia* (cinnamon) bark extract, and *Rheum palmatum* (Chinese rhubarb) as short-term anti-aging agents of the natural extract component. Optionally, other suitable cosmetic adjuvants known in the art may be also added to PreAge. One embodiment of PreAge is shown in the following table:

TABLE 1

| PreAge Ingredients | Percentage by weight (%) |
| --- | --- |
| *Pyrus malus* (apple) fruit extract | 4% |
| *Glycine soja* (soybean) seed extract | 1% |
| *Cinnamomum cassia* (cinnamon) Bark Extract | 1% |
| *Rheum palmatum* (Chinese rhubarb) extract | 1% |
| Butylene Glycol | 93% |
| Total | 100% |

PreAge may be included in the final cosmetic products in the range from about 0.1% to about 5.0% by weight, preferably from about 1.0% to about 4.0% by weight.

TIMP Inducing Agent

Preferably, the composition of the present invention comprises a long-term anti-aging agent. Preferably, the long-term anti-aging effect is provided by at least one TIMP inducing agent. The amount of TIMP inducing agent should be adjusted such that a final cosmetic product comprises from about 0.01% to about 2.00% by weight of a TIMP inducing agent. TIMP inducing agent is a molecule or a complex that enhances the activity of TIMPs and/or up-regulates the production of TIMPs by human body. TIMPs are main regulators of the activity of MMPs. Preferably, the TIMP inducing agent comprises an elastin-derived synthetic peptide acetyl hexapeptide-20. Acetyl hexapeptide-20 of the present invention is able to stimulate the production of endogenous MMP inhibitors (i.e., TIMPs). In addition, acetyl hexapeptide-20 has shown the ability to trigger cellular processes that stimulate human skin fibroblasts proliferation. Fibroblasts synthesize the extracellular matrix including collagen and elastin. When adequately delivered into the dermis, acetyl hexapeptide-20 may mimic basic stimulatory and regulatory steps for collagen and extracellular matrix production, resulting in improvement of aged skin and prevention of intrinsic aging and photo-aging. Without being limited thereto, other suitable TIMP inducing agents may be used in the composition of the present invention.

Preferably, the composition of the present invention comprises a combination of a TIMP inducing agent and a natural extract component for providing long term antioxidative and MMP inhibiting activities. The relevant amounts of each ingredient may be adjusted such that a final cosmetic product comprises from about 0.01% to about 2.00% by weight of a TIMP inducing agent, and from about 1.0% to about 25% by weight of natural extracts. An illustrative example of such combination is Avantage® TE, available from Biocogent, Ltd. Avantage® TE generally comprises acetyl hexapeptide-20 as a TIMP inducing agent, *Tremella fuciformis* (snow fungus) extract as a long-term anti-aging agent of the natural extract component, and *Eugenia caryophyllus* (clove) extract and *Camellia sinensis* (green tea) leaf extract as short-term anti-aging agents of the natural extract component. Optionally, other suitable cosmetic adjuvants known in the art may be also added to this composition. Avantage® TE may be included in the final cosmetic products in the range from about 0.1% to 5% by weight, preferably about 1% to 4% by weight. One embodiment of Avantage® TE is shown in the following table:

TABLE 2

| Avantage ® TE Ingredients | Percentage by weight (%) |
| --- | --- |
| Acetyl Hexapeptide-20 | 1.25% |
| *Tremella fuciformis* (snow fungus) extract | 0.42% |
| *Eugenia caryophyllus* (clove) extract | 4.85% |
| *Camellia sinensis* (green tea) leaf extract | 2.20% |
| Hydrolyzed soy protein | 0.45% |
| Potassium Sorbate | 0.50% |
| Sodium Benzoate | 0.50% |
| Germall 115 | 0.40% |
| Glycerin | 37.5% |
| Water | 51.93% |
| Total | 100% |

Preferably, the composition of the present comprises the combination of PreAge and Avantage® TE. As a result, such a composition comprises an MMP inhibitor component, a TIMP inducing agent, and a natural extract component, which in combination will provide short term and long term antioxidative and MMP inhibiting activities. The ratio between PreAge and Avantage® TE can range from about 99:1 to about 1:99 by weight, preferably from about 9:1 to about 1:9 by weight, and more preferably at about 1:1 by weight. Such combined composition may be incorporated in a final cosmetic product in the range from about 0.1% to about 10%, preferably from about 1.0% to 8.0% by weight, and more preferably from about 2.0% to about 6.0% by weight.

The topical compositions of the present invention may further comprise pH adjusting agents, sunscreens, surfactants, emulsifiers, humectants, emollients, skin conditioning agents, pH preservatives, thickeners, solvents and other acceptable carriers, a mixture thereof, and other cosmetic adjuvants known in the art.

The compositions may also include one or more pH adjusting agents. None limiting examples of pH adjusting agents include ascorbic acid, citric acid, malic acid, sodium citrate, sodium hydroxide, lactic acid, and triethanolamine. In one embodiment of the present invention, 10% citric acid may be used as a pH agent. The pH of the topical compositions of the present invention preferably ranges from about 3.0 to about 8.0.

The composition of the present invention may comprise one or more sunscreens. A wide variety of sun screening agents are described in U.S. Pat. Nos. 5,073,371 and 5,073,372. Non-limiting examples of sunscreens are 2-ethylhexyl p-methoxycinnamate, 2-ethylhexyl N,N-dimethyl-p-aminobenzoate, p-aminobenzoic acid, 2-phenylbenzimidazole-5-sulfonic acid, oxybenzone, octyl salicylate, 4,4'-methoxy-t-butyldibenzolymethane, 3-benzylidene camphor, titanium dioxide, zinc oxide, iron oxide, and mixtures thereof.

The composition of the present invention may comprise one or more surfactants. Surfactants used in the instant invention can be anionic, cationic and amphoteric surfactants. Non-limiting examples of surfactants are alkylbenzene sulfonates, alkane sulfonates, olefin sulfonates, glycerol ether sulfonates, fatty acid isethionates, fatty alcohol/acid polyglycol ethers, alkoxylated triglycerides, polyol fatty acid esters, sugar esters, sorbitan esters, quaternary ammonium compounds, and betaines.

The composition of the present invention may comprise one or more emulsifiers. A wide variety of emulsifiers can be used, but not limited to, those selected from the group consisting of sorbitan esters, glyceryl esters, polyglyceryl esters, methyl glucose esters, sucrose esters, ethoxylated fatty alcohols, hydrogenated castor oil ethoxylates, polymeric emulsifiers and silicone emulsifiers.

The composition of the present invention may comprise one or more emollients. The term emollients, as used herein is intended to include conventional lipid materials (e.g., plant/animal fats, waxes and other water-insoluble materials), polar lipids, hydrocarbons, and silicone oils. Non-limiting examples of conventional emollients are $C_8$-$C_{30}$ alkyl esters of $C_8$-$C_{30}$ carboxylic acids; monoglycerides, diglycerides, and triglycerides of $C_8$-$C_{30}$ carboxylic acids, cholesterol esters of $C_8$-$C_{30}$ carboxylic acids, and hydrocarbons. Also useful as emollients are the so-called "polar lipids" which include $C_{10}$-$C_{20}$ alcohol sorbitan monoesters/diesters/triesters, $C_{10}$-$C_{20}$ fatty alcohol esters of hydroxy acids. Non-limiting examples of silicone emollients are dimethicone copolyol, polysiloxanes, dimethiconol, and mixtures thereof.

The composition of the present invention may comprise one or more humectants. Non-limiting examples of humectants are *Aloe barbadensis* leaf extract, betaines, glycerin, propylene glycol, 1,3-butylene glycol, hydrolyzed corn starch, hydroxylated jojoba oil, lactic acid, lysine PCA, maltose, polyglucuronic acid, *Saccharomyces* lysate extract, sodium PCA, sorbitol, urea, and mixtures thereof.

The composition of the present invention may comprise one or more skin conditioning agents. Non-limiting examples of skin conditioning agents include allantoin, biosaccharide gum, bisabolol, oligopeptides, dimethicone crosspolymer, beta-glucan, sunflower seed oil, linoleic acid, niacin, niacinamide, phospholipids, hydrolyzed soy protein, soy sterol, soy amino acids, sodium hyaluronate, tyrosine, wheat amino acids, and mixtures thereof.

The composition of the present invention may comprise one or more preservatives. Non-limiting examples of preservatives include benzylparaben, butylparaben, chlorhexidine digluconate, diazolidinyl urea, DMDM hydantoin, ethylparaben, imidazolidinyl urea, isobutulparaben, isopropylparaben, Methylparaben, phenyl benzoate, sodium salicylate, triclocarban, triclosan, zinc salicylate and mixtures thereof.

The composition of the present invention may comprise one or more viscosity increasing agents. Viscosity increasing agents can be both aqueous and non-aqueous. Non-limiting examples include acrylamides copolymer, acrylamide/sodium acrylate copolymer, acrylates/alkyl acrylate crosspolymer, beewax, carbomer, cetearyl alcohol, hydrogenated vegetable oils, hydropropyl starch phosphate, magnesium silicate, polyvinyl alcohol, sodium chloride, xanthan gum and mixtures thereof.

The topical compositions of the present invention can be used for the preparation of cosmetic and/or dermapharmaceutical products. Without being limited thereto, the topical composition of the present invention may be in the form of gel, lotion, cream, oil-in-water or water-in-oil emulsions, water-in-silicone emulsions, hydroalcoholic systems, aerosol, spray or anhydrous powder, stick, paste, or viscous liquid. It is contemplated that the topical composition can be applied on any parts of the body except the mucous membranes. Unlimited examples of such body parts to which the topical composition can be properly applied include hands, arms, legs, feet, trunk, and face including eyelids and lips.

The following Examples more fully illustrate selected embodiments of the present invention.

Example 1

Composition Comprising an MMP Inhibitor Component, a TIMP Inducing Agent and a Natural Extract Component The composition according to the present invention providing both short-term and long-term anti-aging effects comprises an MMP inhibitor component, a TIMP inducing agent, and a natural extract component. An example of such MMP-inhibitory and antioxidative complex providing both short-term and long-term effects is shown in Table 3. The relative ranges of amounts of each ingredient in the complex are also provided.

TABLE 3

| Short-Term and Long-Term MMP-Inhibitory and Antioxidative Complex | Percentage Range by Weight (%) |
| --- | --- |
| *Glycine soja* (soybean) seed extract | 0.05%-1.50% |
| Acetyl Hexapeptide-20 | 0.50%-2.50% |
| *Tremella fuciformis* (snow fungus) extract | 0.05%-1.50% |
| *Eugenia caryophyllus* (clove) extract | 0.50%-3.00% |
| *Camellia sinensis* (green tea) leaf extract | 0.50%-2.50% |
| *Cinnamomum cassia* (cinnamon) Bark Extract | 0.05%-1.50% |
| *Pyrus malus* (apple) fruit extract | 1.50%-3.00% |
| *Rheum palmatum* (Chinese rhubarb) extract | 0.05%-1.50% |
| Other ingredients (Solvent, fragrance, preservatives, etc.) | Suitable amount to balance 100% by weight |

The composition according to Table 3 may be incorporated in a final cosmetic product in the range from about 0.1% to about 10%, preferably from about 1.0% to 8.0% by weight, and more preferably from about 2.0% to about 6.0% by weight.

One exemplary embodiment of a MMP-inhibitory and antioxidative complex providing both short-term and long-term effects is shown in Table 4. It was prepared in a conventional manner known in the art.

TABLE 4

| Short-Term and Long-Term MMP-Inhibitory and Antioxidative Complex | Percentage by weight (%) |
| --- | --- |
| *Glycine soja* (soybean) seed extract | 0.500% |
| Acetyl Hexapeptide-20 | 0.625% |
| *Tremella fuciformis* (snow fungus) extract | 0.210% |
| *Eugenia caryophyllus* (clove) extract | 2.425% |
| *Camellia sinensis* (green tea) leaf extract | 1.100% |
| *Cinnamomum cassia* (cinnamon) Bark Extract | 0.500% |
| *Pyrus malus* (apple) fruit extract | 2.000% |
| *Rheum palmatum* (Chinese rhubarb) extract | 0.500% |
| Other ingredients (Solvent, fragrance, preservatives, etc.) | 92.140% |
| Total | 100.000% |

The composition according to Tables 4 may be incorporated in a final cosmetic product in the range from about 0.1% to about 10%, preferably from about 1.0% to about 8.0% by weight, and more preferably from about 2.0% to about 6.0% by weight.

Example 2

Demonstration of MMP Inhibitory Effects of a Composition Comprising an MMP Inhibitor and a Natural Extract Component, a Composition Comprising a TIMP Inducing Agent and a Natural Extract Component, and the Effect of a Combination Thereof in a 1:1 Ratio Using FRET Assay-SensoLyte™

In this test, the relative inhibitory capacities of compositions according to Tables 1, 2, and 4 against MMPs were studied using Fluorescence Resonance Energy Transfer (FRET). FRET has been used for the continuous assay of MMP activity and high-throughput screening of MMP inhibitors. The FRET assay used to analyze the composition according to the present invention was SensoLyte®, available from AnaSpec, Inc. The test utilizes a feature of a FRET peptide (i.e., a generic MMP substrate), which emits fluorescence upon being cleaved by active MMPs. When the cleavage activity of MMPs is inhibited or suppressed by a test composition, (i.e., an MMP inhibitor), no or relatively less fluorescence is detected, depending on the degree of inhibition.

The test was performed in a standard 96-well microplate format. FRET peptides were diluted 1:100 in an assay buffer and added to the 96-well plate (50 μL/well). The composition according to Table 1 ("Complex A") was prepared at concentrations of 1%, 2%, and 4% by weight in the assay buffer. Similarly, the composition according to Table 2 ("Complex B") was prepared at concentrations of 1%, 2%, and 4% by weight in the assay buffer. Finally, the composition of Table 4 ("Complex A+B") was prepared at concentrations of 1%, 2%, and 4% by weight in the assay buffer. The complexes A, B and A+B were each pre-incubated with MMPs and then added to the 96-well plate containing FRET peptides. A positive control (MMPs only) and a substrate control (FRET peptide only) were also prepared as test controls.

The fluorescence of each well was detected by a multi-well microplate fluorometer at Ex/Em=490 nm/520 nm. The fluorescence reading from the substrate control represented the background fluorescence reading, which was subtracted from the readings of other wells to calculate relative fluorescence units (RFU). The data was obtained over a 3.5 hour period.

The experimental results presented in FIG. 1 show that both Complex A (Table 1) and Complex B (Table 2) are powerful inhibitors of MMPs. They demonstrate nearly equivalent inhibitory capacity at the concentrations tested in the assay. When used in the combination at 1:1 ratio by weight (Complex A+B), the composition of Table 4 provides powerful MMP inhibiting effect. In fact, Complex A+B demonstrates a 47.8% increase in MMP inhibition than Complex A alone.

Example 3

Measurements of Anti-Oxidative Effects of a Composition Comprising an MMP Inhibitor and a Natural Extract Component, a Composition Comprising a TIMP Inducing Agent and a Natural Extract Component, and the Effect of a Combination Thereof in a 1:1 Ratio Using μM Copper Reducing Equivalents Antioxidative potentials of compositions according to Tables 1, 2, and 4 were also explored using μM Copper Reducing Equivalents colorimetric assay. The analysis is based on the reduction of $Cu^{2+}$ to $Cu^+$ by the combined action of all the antioxidants presented in each test compositions. A chromogenic reagent, Bathocuproine (2,9-dimethyl-4,7-diphenyl-1,10-phenanthroline) was used to selectively detect $Cu^+$ at the absorbance of wavelength 480 to 490 nm.

The composition according to Table 1 ("Complex A"), Table 2 ("Complex B"), and Table 4 ("Complex A+B") were each prepared in a well at concentrations of 1%, 2%, and 5%, and their absorbances at 490 nm were taken individually. A $Cu^{2+}$ solution was then added to each well, followed by incubation at room temperature. After 3 minutes of incubation, absorbance of each well was again taken at 490 nm, and the difference between the absorbance readings before and after the incubation was calculated.

Antioxidant capacities of the test compositions were calculated using a set of uric acid standard curves having the difference of absorbance readings as vertical axis and concentration of uric acid standards (mM) as horizontal axis. The difference in absorbance readings in each test composition was used to calculate the corresponding uric acid standard concentration (mM). Each uric acid standard concentration was converted to "μM Copper Reducing Equivalents" based on the relationship 1 mM of uric acid=2189 μM $Cu^{2+}$ to $Cu^+$ (copper reducing power).

Figure 2:
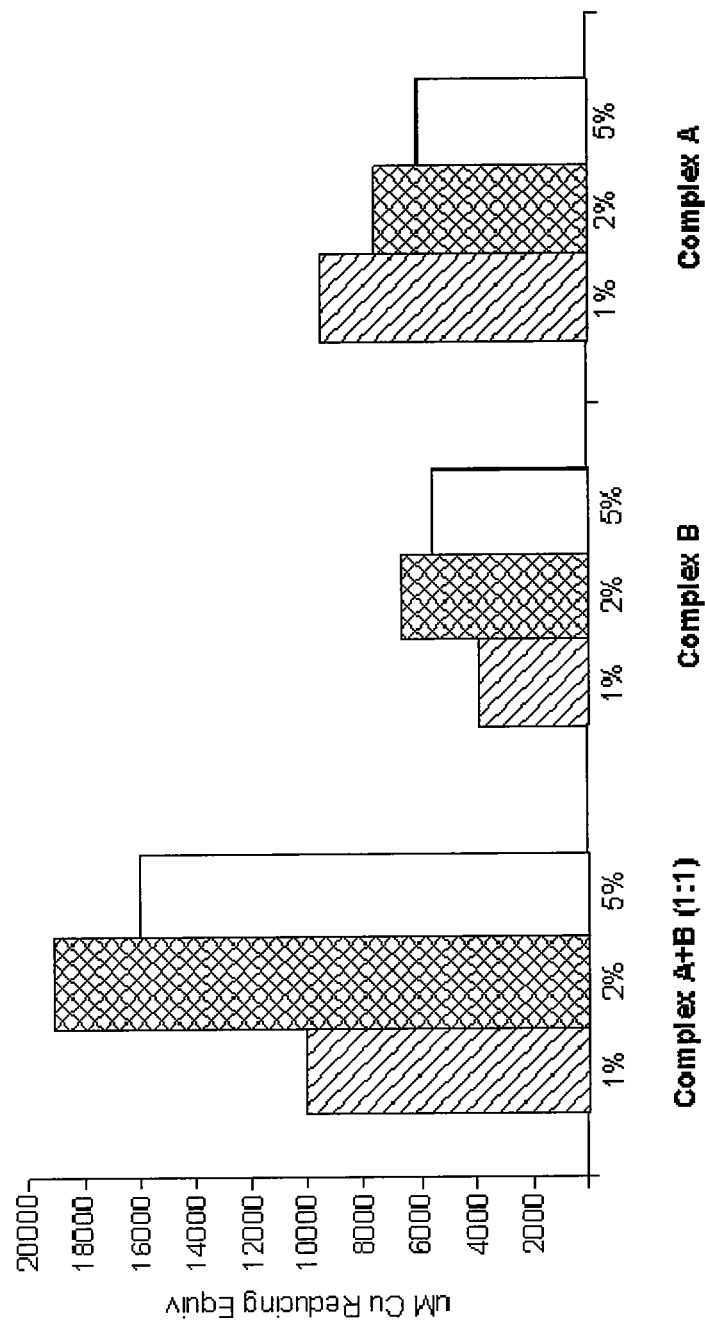
FIG. 2 illustrates a histogram representing the total antioxidant potential (TAOP) of a composition comprising an MMP inhibitor and natural extracts, a composition comprising a TIMP inducing agent and natural extracts, and the effect of a combination thereof in a 1:1 ratio.

As seen in FIG. 2, the results of the test using Complex A, Complex B and Complex A+B in 1%, 2%, and 5% concentrations were expressed as "μM Copper Reducing Equivalents." Here, the higher the μM Copper Reducing Equivalents, the greater the total antioxidant potential. FIG. 2 shows that the composition of Complex B (Table 2) and Complex A (Table 1) both demonstrate potent antioxidant activity. The antioxidant activity of these two candidates is equivalent on a weight percent basis. When Complexes A and B are combined in a 1:1 ratio (Complex A+B), the antioxidative activity is 12.6% greater than that of the theoretical combination of the two. At the use level of 2% by weight, Complex A+B provides more than twice the antioxidant activity than Complex A alone.

Example 4

Formulation Example of a Serum Composition

| INCI Name | % Active in Finished Product |
|---|---|
| *Glycine Soja* (Soybean) Seed Extract | 0.010 |
| Acetyl Hexapeptide-20 | 0.030 |
| *Pyrus Malus* (Apple) Fruit Extract | 0.040 |
| *Cinnamomum Cassia* Bark Extract | 0.010 |
| *Rheum Palmatum* Extract | 0.010 |
| *Tremella Fuciformis* (Mushroom) Extract | 0.010 |
| *Eugenia Caryophyllus* (Clove) Flower Extract | 0.030 |
| *Camellia Sinensis* Leaf Extract | 0.030 |
| Soy Amino Acids | 0.030 |
| Butylene Glycol | 2.395 |
| Glycerin | 0.300 |
| Imidazolidinyl Urea | 0.004 |
| Potassium Sorbate | 0.001 |
| Sodium Benzoate | 0.005 |
| Citric Acid | 0.005 |
| C12-20 Alkyl Glucoside | 0.600 |
| Benzoic Acid | 0.200 |
| BHA | 0.002 |
| BHT | 0.007 |
| C14-22 Alcohols | 2.400 |
| Caprylyl Glycol | 0.250 |
| Caprylyl Methicone | 1.500 |
| Carnosine | 0.200 |
| Castor Isostearate Succinate | 0.500 |
| Cetyl Dimethicone | 2.000 |
| Ethylhexylglycerin | 0.150 |
| Fragrance (Parfum) | 0.250 |
| Hexylene Glycol | 0.100 |
| Hydrogenated Starch Hydrolysate | 0.540 |
| Hydroxyphenyl Propamidobenzoic Acid | 0.050 |
| Lecithin | 0.090 |
| Maltooligosyl Glucoside | 0.940 |
| Myristyl Nicotinate | 1.000 |
| Neopentyl Glycol Diheptanoate | 6.000 |
| Palm Alcohol | 0.250 |
| Pentylene Glycol | 0.975 |
| Phenoxyethanol | 0.515 |
| Phytosteryl Canolate | 0.030 |
| Polyacrylate-13 | 0.750 |
| Polyglyceryl-10 Distearate | 0.700 |
| Polyisobutene | 0.375 |

-continued

| INCI Name | % Active in Finished Product |
|---|---|
| Polymethyl Methacrylate | 1.000 |
| Polysorbate 20 | 0.176 |
| Retinol | 0.099 |
| *Rosa Multiflora* Fruit Extract | 0.005 |
| Sodium Hyaluronate | 0.010 |
| Sodium Polyacrylate | 0.100 |
| Tetrahexyldecyl Ascorbate | 0.300 |
| Tocopheryl Acetate | 0.500 |
| *Triticum Vulgare* (Wheat) Germ Extract | 0.500 |
| Vegetable Oil (Olus) | 0.620 |
| Water (Aqua) | 73.406 |
| TOTAL | 100.000 |

Example 5

Formulation Example of an Eye Cream Composition

| INCI Name | % Active in Finished Product |
|---|---|
| *Glycine Soja* (Soybean) Seed Extract | 0.010 |
| Acetyl Hexapeptide-20 | 0.030 |
| *Pyrus Malus* (Apple) Fruit Extract | 0.040 |
| *Cinnamomum Cassia* Bark Extract | 0.010 |
| *Rheum Palmatum* Extract | 0.010 |
| *Tremella Fuciformis* (Mushroom) Extract | 0.010 |
| *Eugenia Caryophyllus* (Clove) Flower Extract | 0.030 |
| *Camellia Sinensis* Leaf Extract | 0.030 |
| Soy Amino Acids | 0.030 |
| Butylene Glycol | 3.780 |
| Glycerin | 0.800 |
| Imidazolidinyl Urea | 0.004 |
| Potassium Sorbate | 0.001 |
| Sodium Benzoate | 0.005 |
| Citric Acid | 0.005 |
| Alcohol | 0.140 |
| *Aloe Barbadensis* Leaf Juice Powder | 0.911 |
| BHA | 0.001 |
| BHT | 0.003 |
| C12-20 Alkyl Glucoside | 0.600 |
| C14-22 Alcohols | 2.400 |
| Caprylyl Glycol | 0.290 |
| Caprylyl Methicone | 2.500 |
| Castor Isostearate Succinate | 0.500 |
| Cetyl Dimethicone | 4.000 |
| Disodium EDTA | 0.024 |
| Ethylhexylglycerin | 0.125 |
| Fragrance | 0.500 |
| *Glycine Soja* (Soybean) Sterols | 0.500 |
| *Halidrys Siliquosa* Extract | 1.000 |
| Hexylene Glycol | 0.125 |
| Hyaluronic acid | 0.500 |
| Hydrogenated Starch Hydrolysate | 0.540 |
| Lecithin | 0.180 |
| *Lilium Candidum* Flower Extract | 0.350 |
| Magnesium Ascorbyl Phosphate | 0.080 |
| *Mallotus Japonicus* Bark Extract | 0.040 |
| Maltodextrin | 0.003 |
| Maltooligosyl Glucoside | 0.940 |
| Methylparaben | 0.005 |
| Methylsilanol Hydroxyproline Aspartate | 3.946 |
| Neopentyl Glycol Diheptanoate | 6.000 |
| Palm Alcohol | 0.500 |
| PEG-40 Hydrogenated Castor Oil | 1.150 |
| *Pfaffia Paniculata* Root Extract | 0.800 |
| Phenoxyethanol | 0.629 |
| Phytosteryl Canolate | 0.060 |

-continued

| INCI Name | % Active in Finished Product |
|---|---|
| *Piptadenia Colubrina* Peel Extract | 0.650 |
| Polyacrylate-13 | 1.080 |
| Polyglyceryl-10 Distearate | 1.200 |
| Polyisobutene | 0.540 |
| Polymethyl Methacrylate | 1.000 |
| Polysorbate 20 | 0.146 |
| Potassium Sorbate | 0.036 |
| *Ptychopetalum Olaciodes* Bark/Stem Extract | 0.750 |
| Retinol | 0.050 |
| *Rubus Idaeus* (Raspberry) Leaf Extract | 0.005 |
| Salicylic Acid | 0.012 |
| Sodium Benzoate | 0.206 |
| Sodium Polyacrylate | 0.100 |
| Tetrahexyldecyl Ascorbate | 1.000 |
| Tetrapeptide-21 | 0.002 |
| Tocopheryl Acetate | 1.000 |
| Vegetable Oil (Olus) | 1.240 |
| Water (Aqua) | 56.846 |
| TOTAL | 100.000 |

Example 6

Formulation Example of a Skin Moisturizer Composition

| INCI Names | % Active in Finished Product |
|---|---|
| *Glycine Soja* (Soybean) Seed Extract | 0.003 |
| Acetyl Hexapeptide-20 | 0.025 |
| *Pyrus Malus* (Apple) Fruit Extract | 0.050 |
| *Cinnamomum Cassia* Bark Extract | 0.003 |
| *Rheum Palmatum* Extract | 0.003 |
| *Tremella Fuciformis* (Mushroom) Extract | 0.005 |
| *Eugenia Carophyllus* (Clove) Flower Extract | 0.025 |
| *Camellia Sinensis* (Green Tea) Leaf Extract | 0.025 |
| Soy Amino Acids | 0.020 |
| Butylene Glycol | 1.911 |
| Glycerin | 3.991 |
| Aluminum Oxide | 0.228 |
| Ascorbyl Palmitate | 0.100 |
| Benzylidene Dimethoxydimethylindanone | 0.500 |
| Bisabolol | 0.099 |
| Calcium Pantothenate | 0.009 |
| Caprylic/Capric Triglyceride | 3.526 |
| Caprylyl Glycol | 0.445 |
| Caprylyl Methicone | 2.000 |
| Carnosine | 0.050 |
| Cetyl Alcohol | 1.750 |
| Diisostearyl Dimer Dilinoleate | 1.250 |
| Dimethicone | 1.500 |
| Disodium EDTA | 0.050 |
| Dithiaoctanediol | 0.020 |
| Ethylhexylglycerin | 0.250 |
| Fragrance | 0.400 |
| Gluconic Acid | 0.020 |
| Glyceryl Acrylate/Acrylic Acid Copolymer | 0.024 |
| Glyceryl Oleate Citrate | 1.038 |
| Glyceryl Stearate | 3.300 |
| Homosalate | 8.000 |
| Hydrolyzed Oat Protein | 0.123 |
| Hydroxyphenyl Propamidobenzoic Acid | 0.002 |
| Hydroxypropyl Starch Phosphate | 1.500 |
| Isostearic Acid | 0.169 |
| Lecithin | 0.189 |
| Magnesium Ascorbyl Phosphate | 0.009 |
| Magnesium Salicylate | 0.009 |

-continued

| INCI Names | % Active in Finished Product |
|---|---|
| Octinoxate | 7.500 |
| Octisalate | 5.000 |
| Octyldodecanol | 1.750 |
| Panthenol | 0.009 |
| PEG-100 Stearate | 1.800 |
| Pentylene Glycol | 0.949 |
| Phenoxyethanol | 0.555 |
| Phopholipids | 0.009 |
| Polyglyceryl-3 Polyricinoleate | 0.153 |
| Polyhydroxystearic Acid | 0.073 |
| Polyhydroxystearic Acid | 0.080 |
| Preservatives | 0.003 |
| PVM/MA copolymer | 0.013 |
| Stearic Acid | 0.132 |
| Sutilains | 0.001 |
| Titanium Dioxide | 1.840 |
| Xanthan Gum | 0.430 |
| Zinc Gluconate | 0.009 |
| Zinc Oxide | 5.075 |
| *Zinger Officinale* (Ginger) Root Extract | 0.001 |
| Water (Aqua) | 41.997 |
| TOTAL | 100.000 |

Example 7

Formulation Example of a Serum Lotion Composition

| INCI Name | % Active in Finished Product |
|---|---|
| *Glycine Soja* (Soybean) Seed Extract | 0.003 |
| Acetyl Hexapeptide-20 | 0.025 |
| *Pyrus Malus* (Apple) Fruit Extract | 0.050 |
| *Cinnamomum Cassia* Bark Extract | 0.003 |
| *Rheum Palmatum* Extract | 0.003 |
| *Tremella Fuciformis* (Mushroom) Extract | 0.005 |
| *Eugenia Carophyllus* (Clove) Flower Extract | 0.025 |
| *Camellia Sinensis* (Green Tea) Leaf Extract | 0.025 |
| *Acer Saccharum* (Sugar Maple) Extract | 0.010 |
| *Avena Sativa* (Oat) Kernel Extract | 0.001 |
| Soy Amino Acids | 0.020 |
| Butylene Glycol | 7.390 |
| Glycerin | 0.425 |
| Betaine | 0.800 |
| Caprylic/Capric Triglyceride | 1.750 |
| Caprylyl Methicone | 1.000 |
| Cetearyl Alcohol | 2.800 |
| Ceteth-10 Phosphate | 0.600 |
| Cetyl Alcohol | 0.500 |
| *Citrus Aurantium Dulcis* (Orange) Fruit Extract | 0.010 |
| *Citrus Medica Limonum* (Lemon) Fruit Extract | 0.010 |
| Dicetyl Phosphate | 0.600 |
| Ethylhexylglycerin | 0.250 |
| Fragrance | 0.250 |
| Glycolic Acid | 2.800 |
| Hydrolyzed Lupine Protein | 0.100 |
| Hydrolyzed Sclerotium Gum | 0.080 |
| Hydroxyphenyl Propamidobenzoic Acid | 0.100 |
| *Lactobacillus* Ferment Filtrate | 4.000 |
| Methylisothiazolinone | 0.007 |
| Octyldodecanol | 1.750 |
| Pentylene Glycol | 0.950 |
| Phenethyl Alcohol | 0.065 |
| Polyglutamic Acid | 0.070 |
| Potassium Lactate | 0.220 |
| PPG-14 Butyl Ether | 5.000 |

-continued

| INCI Name | % Active in Finished Product |
|---|---|
| PPG-2 Methyl Ether | 0.039 |
| *Saccharum Officinarum* (Sugar Cane) Extract | 0.010 |
| Salicylic Acid | 1.000 |
| Sucrose | 0.500 |
| Tetrahexyldecyl Ascorbate | 0.100 |
| Triethanolamine | 2.079 |
| Urea | 0.475 |
| *Vaccinium Myrtillus* Fruit/Leaf Extract | 0.010 |
| Water (Aqua) | 63.240 |
| Xanthan Gum | 0.600 |
| Yogurt Powder | 0.250 |
| TOTAL | 100.000 |

Example 8

Formulation Example of a Night Cream Composition

| INCI Name | % Active in Finished Product |
|---|---|
| *Glycine Soja* (Soybean) Seed Extract | 0.007 |
| Acetyl Hexapeptide-20 | 0.050 |
| *Pyrus Malus* (Apple) Fruit Extract | 0.100 |
| *Cinnamomum Cassia* Bark Extract | 0.007 |
| *Rheum Palmatum* Extract | 0.007 |
| *Tremella Fuciformis* (Mushroom) Extract | 0.010 |
| *Eugenia Carophyllus* (Clove) Flower Extract | 0.050 |
| *Camellia Sinensis* (Green Tea) Leaf Extract | 0.050 |
| Soy Amino Acids | 0.040 |
| Butylene Glycol | 7.346 |
| Glycerin | 3.409 |
| Ascorbyl Palmitate | 0.100 |
| Behenyl Alcohol | 1.000 |
| Bisabolol | 0.200 |
| *Butyrospermum Parkii* (Shea Butter) Unsaponifiables | 0.750 |
| *Caesalpinia Spinosa* Gum | 0.011 |
| Caffeine | 0.100 |
| Calcium Pantothenate | 0.030 |
| Caprylyl Glycol | 0.445 |
| Carnosine | 0.050 |
| Cetearyl Alcohol | 4.400 |
| Cetearyl Glucoside | 0.600 |
| Cholesterol | 0.100 |
| Dicapryl Succinate | 3.000 |
| Dimethicone | 1.000 |
| Disodium EDTA | 0.050 |
| Dithiaoctanediol | 0.020 |
| Ethylhexylglycerin | 0.250 |
| Fragrance | 0.200 |
| Gluconic Acid | 0.020 |
| Glyceryl Acrylate/Acrylic Acid Copolymer | 0.018 |
| Hydrogenated Lecithin | 0.500 |
| Hydrogenated Polydecene | 0.300 |
| Hydrolyzed *Caesalpinia Spinosa* Gum | 0.045 |
| Hydrolyzed Oat Protein | 0.410 |
| Hydroxyphenyl Propamidobenzoic Acid | 0.002 |
| Isostearyl Neopentanoate | 0.900 |
| Magnesium Ascorbyl Phosphate | 0.030 |
| Magnesium Salicylate | 0.030 |
| Methyl Glucose Sesquistearate | 0.650 |
| Panthenol | 0.030 |
| Pentylene Glycol | 2.949 |
| Phenoxyethanol | 0.555 |
| Phopholipids | 0.030 |
| Preservatives | 0.011 |
| PVM/MA Copolymer | 0.009 |

-continued

| INCI Name | % Active in Finished Product |
|---|---|
| Sodium Acrylate/Sodium Acryloyldimethyl Taurate Copolymer | 0.470 |
| Sodium Citrate | 0.100 |
| Sodium Hyaluronate | 0.008 |
| Sorbitan Laurate | 0.150 |
| Soybean Glycerides | 2.250 |
| Squalane | 1.000 |
| Stearic Acid | 0.750 |
| Sugar | 1.000 |
| Sutilains | 0.001 |
| Trideceth-6 | 0.080 |
| Water (Aqua) | 63.989 |
| Xanthan Gum | 0.300 |
| Zinc Gluconate | 0.030 |
| *Zinger Officinale* (Ginger) Root Extract | 0.001 |
| TOTAL | 100.000 |

Example 9

Formulation Example of a Renewing Serum Composition

| INCI Name | % Active in Finished Product |
|---|---|
| *Glycine Soja* (Soybean) Seed Extract | 0.003 |
| Acetyl Hexapeptide-20 | 0.025 |
| *Pyrus Malus* (Apple) Fruit Extract | 0.050 |
| *Cinnamomum Cassia* Bark Extract | 0.003 |
| *Rheum Palmatum* Extract | 0.003 |
| *Tremella Fuciformis* (Mushroom) Extract | 0.005 |
| *Eugenia Carophyllus* (Clove) Flower Extract | 0.025 |
| *Camellia Sinensis* (Green Tea) Leaf Extract | 0.025 |
| Soy Amino Acids | 0.020 |
| Butylene Glycol | 4.889 |
| Glycerin | 2.643 |
| Ascorbyl Palmitate | 0.100 |
| Bifida Ferment Lysate | 0.030 |
| Bisabolol | 0.199 |
| Bis-PEG-18 Methyl Ether Dimethyl Silane | 2.000 |
| Caffeine | 0.200 |
| Calcium Pantothenate | 0.030 |
| Caprylic/Capric Triglyceride | 0.150 |
| Caprylyl Glycol | 0.445 |
| Carnosine | 0.100 |
| Cholesterol | 0.100 |
| Cyclopentasiloxane | 6.000 |
| Dimethicone | 0.100 |
| Disodium EDTA | 0.100 |
| Dithiaoctanediol | 0.020 |
| Ethylhexylglycerin | 0.250 |
| Fragrance | 0.250 |
| Gluconic Acid | 0.020 |
| *Hordeum Distichon* (Barley) Extract | 0.300 |
| Hydrogenated Lecithin | 0.300 |
| Hydrolyzed Oat Protein | 0.410 |
| Hydroxyethyl Acrylate/Sodium Acryloyldimethyl Taurate Copolymer | 0.620 |
| Hydroxyphenyl Propamidobenzoic Acid | 0.002 |
| Isohexadecane | 0.434 |
| Lactose | 0.090 |
| Magnesium Ascorbyl Phosphate | 0.030 |
| Magnesium Salicylate | 0.030 |
| Methyl Gluceth-20 | 0.750 |
| Mica | 0.500 |
| Milk Protein | 0.060 |
| *Olea Europaea* (Olive) Fruit Oil | 0.250 |

-continued

| INCI Name | % Active in Finished Product |
|---|---|
| Panthenol | 0.030 |
| PEG-40 Hydrogenated Castor Oil | 1.000 |
| Pentylene Glycol | 0.949 |
| *Phellodendron Amurense* Bark Extract | 0.100 |
| Phenoxyethanol | 0.555 |
| Phopholipids | 0.036 |
| Polysorbate 60 | 0.124 |
| Preservatives | 0.003 |
| *Santalum Album* (Sandalwood) Extract | 0.100 |
| Silica | 1.250 |
| Sodium Hyaluronate | 0.015 |
| Water (Aqua) | 73.996 |
| Xanthan Gum | 0.250 |
| Zinc Gluconate | 0.030 |
| *Zinger Officinale* (Ginger) Root Extract | 0.001 |
| TOTAL | 100.000 |

While the present invention has been described with reference to the preferred embodiment and alternative embodiments, which have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. A topical skin composition comprising:

(a) a soybean seed extract at a concentration of 0.1-0.9% by weight;

(b) a reaction product of acetic acid and a hexapeptide consisting of alanine, glycine, valine, and proline at a concentration of 0.125-1.125% by weight;

(c) apple fruit extract at a concentration of 0.4-3.6% by weight;

(d) cinnamon bark extract at a concentration of 0.1-0.9% by weight;

(e) Chinese rhubarb extract at a concentration of 0.1-0.9% by weight;

(f) snow fungus extract at a concentration of 0.042-0.378% by weight;

(g) clove extract at a concentration of 0.485-4.365% by weight; and (h) green tea leaf extract at a concentration of 0.22-1.98% by weight.

2. A cosmetic product comprising, the composition of claim 1 at a concentration of 0.1-10% by weight.

3. A cosmetic product comprising the composition of claim 1 at a concentration of 1.0-8.0% by weight.

4. A cosmetic product comprising the composition of claim 1 at a concentration of 2.0-6% by weight.

5. A method for providing antioxidant and matrix metalloprotease inhibiting activities to the skin, comprising the steps of: topically applying the product of claim 2.

6. A topical skin composition comprising:
   (a) a soybean seed extract at a concentration of about 0.5% by weight;
   (b) a reaction product of acetic acid and a hexapeptide consisting of alanine, glycine, valine, and proline at a concentration of about 0.625% by weight;
   (c) apple fruit extract at a concentration of about 2.000% by weight;
   (d) cinnamon bark extract at a concentration of about 0.500% by weight;
   (e) Chinese rhubarb extract at a concentration of about 0.500% by weight;
   (f) snow fungus extract at a concentration of about 0.210% by weight;
   (g) clove extract at a concentration of about 2.425% by weight; and
   (h) green tea leaf extract at a concentration of about 1.100% by weight.

7. A cosmetic product comprising the composition of claim 6 at a concentration of 0.1-10% by weight.

8. A cosmetic product comprising the composition of claim 6 at a concentration of 1.0-8.0% by weight.

9. A cosmetic product comprising the composition of claim 6 at a concentration of 2.0-6% by weight.

10. A method for providing antioxidant and matrix metalloprotease inhibiting activities to the skin, comprising the steps of: topically applying the composition of claim 6.

11. A method for providing antioxidant and matrix metalloprotease inhibiting activities to the skin, comprising the steps of topically applying the product of claim 7.

* * * * *